United States Patent [19]

Ognier et al.

[11] Patent Number: 4,924,851
[45] Date of Patent: May 15, 1990

[54] SURGICAL APPARATUS

[75] Inventors: Jean-Francois Ognier, Saignes; Hubert Manhes, Uicety, both of France

[73] Assignee: Societe dite Sinergy S.A., Cusset, France

[21] Appl. No.: 293,935

[22] Filed: Jan. 5, 1989

[30] Foreign Application Priority Data

Jan. 5, 1988 [FR] France ................ 88 00170

[51] Int. Cl.⁵ .............................................. A61B 1/00
[52] U.S. Cl. ...................................... 128/4; 604/264
[58] Field of Search .................... 128/4, 6; 604/264

[56] References Cited

U.S. PATENT DOCUMENTS

| | | | |
|---|---|---|---|
| 3,902,495 | 9/1975 | Weiss et al. | 604/22 |
| 3,920,014 | 11/1975 | Banko | 604/31 |
| 3,990,456 | 11/1976 | Iglesias | 128/303.15 |
| 4,030,502 | 6/1977 | Iglesias | 128/303.15 |
| 4,614,625 | 9/1986 | Wilson | 264/6 |

FOREIGN PATENT DOCUMENTS 2474857 12/1986 France .

*Primary Examiner*—William H. Grieb
*Attorney, Agent, or Firm*—Curtis, Morris & Safford

[57] ABSTRACT

Operative coelioscopy surgical apparatus for receiving electrical instruments, flexible mechanical instruments and rigid mechanical instruments. The apparatus includes a tubular canula and a handle member which is removably attached to the canula by a bayonet-type connection. The handle is provided with a series of control members which may be operated either simultaneously or separately, and these comprise a first push-button for controlling the transmission of irrigation fluids through the canula, a second push-button for controlling the aspiration of irrigation or body fluids through the canula, a third push-button for supplying electrical power and a lever member for mechanically controlling the movement of rigid and flexible instruments.

11 Claims, 6 Drawing Sheets

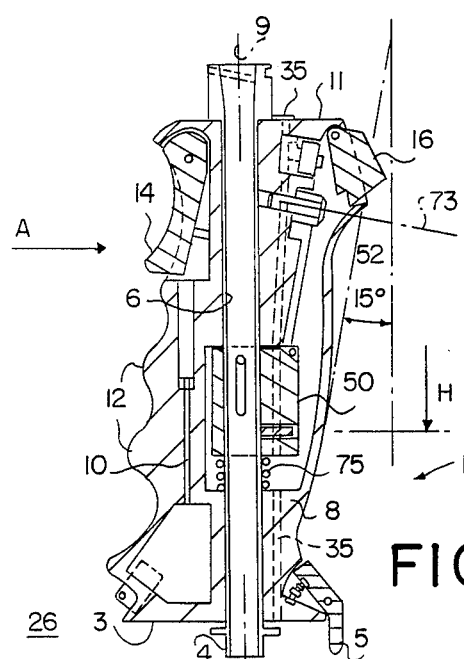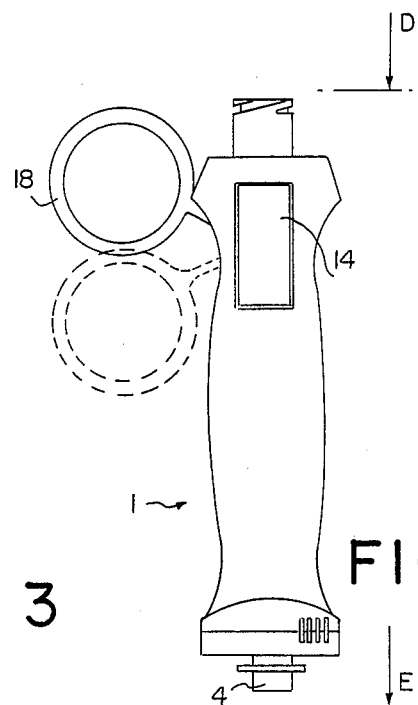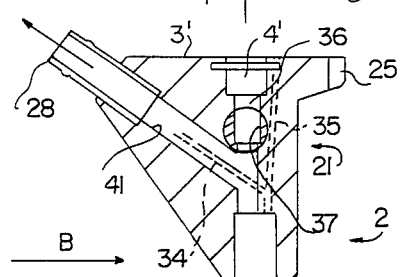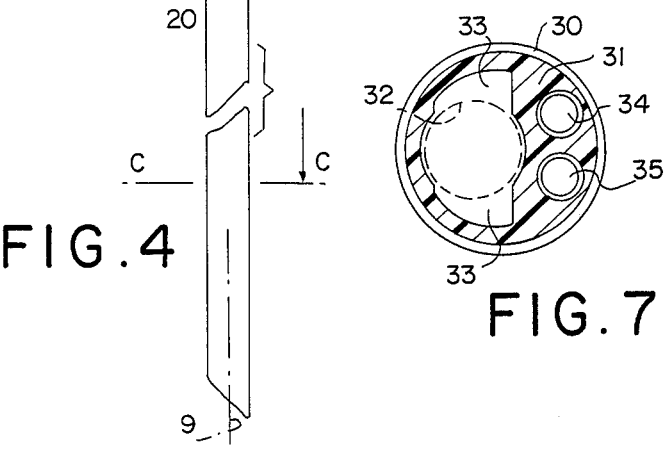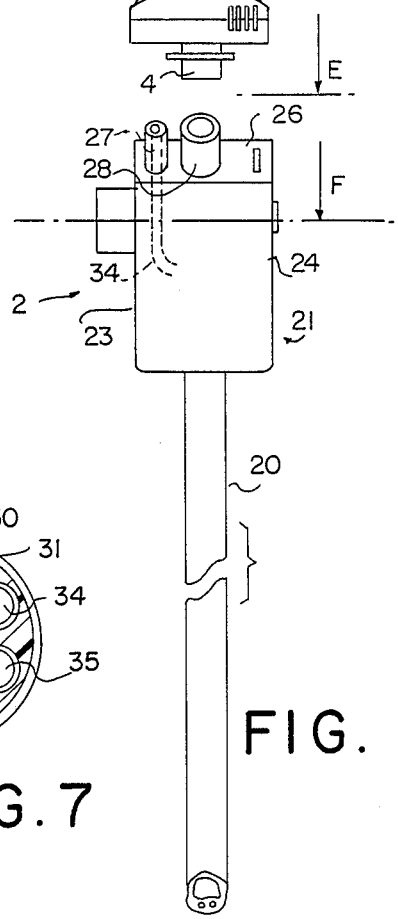

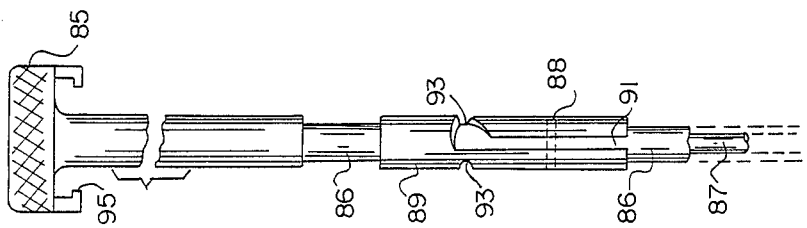
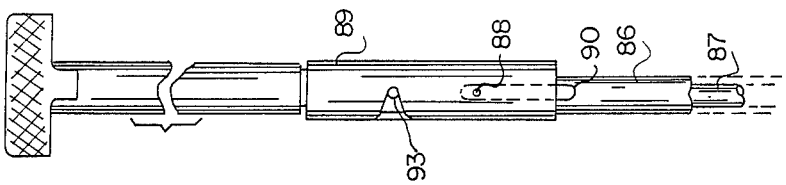
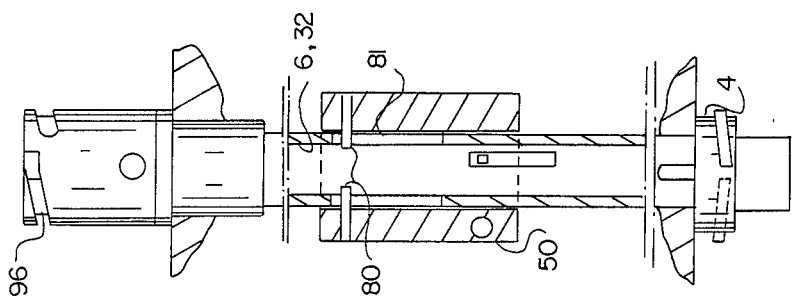
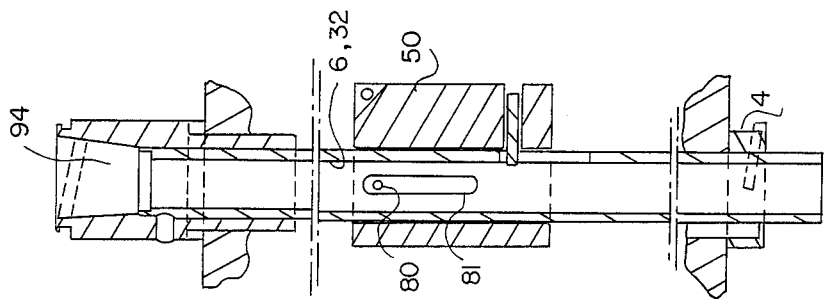

SURGICAL APPARATUS

BACKGROUND OF THE INVENTION

The present invention is in the field of surgical apparatus and relates to a multi-functional instrument for operations of endoscopic surgery, also known as coelioscopic surgery.

The publication FR No. 2,474,857 (Ets BOUTMY, Inv. MANHES) has disclosed a multi-functional surgical apparatus comprising a tube combining space for fluid circulation and a space for guidance for surgical instruments, the space for fluid circulation being subdivided into a plurality of sub-spaces including at least one liquid aspiration duct. A tube, known as a canula, is introduced into this apparatus in the vicinity of one of its ends, in a casing forming a handle for manipulation; lateral nozzles debouch into the canula at the level of the handle; still at the level of the handle, it is possible to introduce into the canula an instrument such as an electrical bistoury. This apparatus of the prior art has proven its effectiveness; however, its use has revealed a number of disadvantages or inadequacies. For example, the number of functions is restricted to three (incision, irrigation, aspiration), it is difficult to sterilize because of the need to heat the entire apparatus to 200° C., and it often requires multiplying the number of incisions for the introduction of other instruments (scissors, forceps, lasers, electrocoagulators, etc.).

In order to understand the background to the technology proposed by the present invention, it is also possible to refer to the following publications: U.S. Pat. No. 3,902,495 which describes a device for monitoring and controlling an aspiration system, U.S. Pat. No. 3,920,014 which describes a surgical device making it possible to monitor the irrigation and aspiration of fluids, U.S. Pat. Nos. 3,990,456 and 4,030,502 which describe resectoscopes having bipolar electrodes for urinary tracts, and finally U.S. Pat. No. 4,614,625 which describes a gastric canula.

SUMMARY

The general object of the present invention, in the light of the experience gained in use of the apparatus invented by MANHES and by virtue of the development of associated techniques and novel materials which have appeared on the market, is to propose an improved surgical apparatus aimed at overcoming the disadvantages and inadequacies encountered with the abovementioned apparatus.

A first specific object of the invention is to make available to the surgeon a highly ergonomic apparatus which facilitates the surgeon's manipulations and improves the accuracy of his actions.

A second specific object of the invention is to propose an apparatus which is easy to clean and sterilize as regards its parts which come in direct or indirect contact with the tissues of the organism.

A third specific object is to propose an apparatus which permits the rapid and accurate adaptation and employment of a wide variety of surgical instruments (forceps, bistoury, etc.) or instruments of observation (optical coelioscope, microcamera, etc...).

Thus, and according to the present invention, there is provided a surgical apparatus intended for operative coelioscopy, called a multi-functional instrument, of the type formed of a tube, or canula, within which various instruments can be introduced. The tube allows the passage of bodily liquids or irrigation liquids and has in the vicinity of the outer end an operating and connecting handle. The apparatus comprises the following arrangements, taken separately or in combination:

- the canula is a part which can be separated from the handle;
- the handle bears a plurality of means of controlling the various functions, which can be actuated simultaneously or separately by two fingers of the same hand, namely:
    - first and second means for the electrical control of the transmission of irrigation liquid on the one hand, and aspiration of the irrigation liquid or of bodily liquids on the other hand,
    - third means for the electrical control either of a thermal or electrical coagulator or of a surgical laser,
    - fourth means for the mechanical control of rigid instruments, referred to as specific instruments, and/or instruments referred to as flexible.

The apparatus can simultaneously receive instruments referred to as flexible (monopolar electrocoagulating tip, cutting blade, laser beam-conducting optical fiber, etc.) and rigid instruments which can either be conventional instruments (forceps, scissors, $CO_2$ laser, sealed puncture, etc...) having their own means of manipulation, or instruments referred to as specific, designed to be manipulated from the handle.

According to an embodiment, the abovementioned tube is constituted of at least two parts: the first part surrounded by the handle as such, and the second part forming the canula as such, it being possible for the two parts to be connected to one another in their axial extension, or alternatively, to be separated from one another. The result of the arrangement is that the second part, which will be the part in direct or indirect contact with the tissues, can be cleaned and sterilized separately from the first, as a consequence of which the first part can be of some complexity as regards its mechanical or electrical components.

Advantageously, the handle is connected to the canula by means of a "quarter-turn" bayonet connector and helical ramp, a ratchet-locking mechanism ensuring that the two parts of the apparatus are maintained in the connected position.

In a general manner, again, the canula possesses at least three ducts along its axis; an irrigation duct, a duct for the passage of flexible smalldiameter cutting instruments, and an axial duct for guiding rigid instruments, which can also form an evacuation duct. Moreover, the canula is integral with a piece referred to as a connecting piece, having approximately the general shape of a polygonal based prism and possessing a plurality of lateral faces and two base faces, one of the lateral faces perpendicular to the axis of the canula constituting a face for connection to the handle.

Advantageously, the axial duct forks in the connecting part into an axial duct emerging at the connecting face and into a lateral evacuation duct emerging in the first nozzle on a first lateral face, called the branching face, of the connecting part; advantageously, again, a slide valve which can alternatively close or open the passage into the axial duct is arranged across the axial duct, the axis of the slide of the valve being perpendicular to the axis of the axial duct and sufficiently close to the abovementioned fork not to create a dead retention space. A clack-valve situated in the second nozzle, referred to as the irrigation inlet nozzle, renders the passage of liquid mono-directional in the direction of the canula, while guaranteeing a minimum irrigation pressure which can give rise to a jet intended to detach and remove organic particles.

Advantageously, the guiding duct is a cylindrical part of the axial duct and possesses, laterally, at least one eccentric part forming the evacuation duct which terminates in the lateral evacuation duct.

Advantageously again, the duct for the passage of flexible instruments terminates at the said connecting face, coinciding, when the two parts of the apparatus are joined, with its extension into the handle as far as its termination at an upper end of the latter.

According to another general provision of the invention, the handle has the general shape of an elongated parallelepiped. One of the base faces of the handle constitutes a connecting face and is perpendicular to the said first part of the tube. The axis of the handle is inclined at about 15° relative to the axis of the tube, and at least one push-button is provided on the posterior face of the handle while another push-button, referred to as a detent, is provided on the anterior face of the handle. The push-buttons and detent one situated in the vicinity of the upper end of the latter, while an operating lever is provided on one of the lateral faces of the handle in the vicinity of the upper end of the latter.

Of the push-buttons, referred to above as first and second control means, preferably numbering two and arranged side by side, one is intended to control an irrigation solenoid and the other to control an aspiration solenoid. The push-buttons are accessible to the thumb, separately or simultaneously.

The detent, referred to above as the third control means, is accessible to the index finger. It is intended to control the connection to power or the functioning of various electrical accessories or apparatus.

The lever constituting the abovementioned fourth means of mechanical control is intended for the manual manipulation of a rigid instrument, referred to as a specific instrument, placed in the guiding duct and/or of a flexible instrument placed in the passage duct. The lever is connected to a slider surrounding the said first part of the tube in an appropriate seating in the handle, with a view to imparting, via the slider and at least one internal pin of the latter passing through a longitudinal port made in the tube, an axial movement to a specific rigid instrument placed in the tube.

The slider, which itself is pierced axially in the extension of the said duct for the passage of flexible instruments, supports a coupling mechanism intended to permit the coupling thereto of a flexible instrument passing into the passage duct, and to permit the reciprocal movement of the said flexible instrument under the control of the lever, or, possibly, to uncouple the flexible instrument from the slider in the event of the presence in the tube of rigid instruments which are incompatible with the flexible instrument, the coupling or uncoupling being performed by a sensor finger which projects through a port in the tube.

BRIEF DESCRIPTION OF THE DRAWINGS

The present invention will be better understood and details thereof will become apparent from the description of an embodiment which follows and which is given in relation to the figures of the attached drawings, in which:

FIGS. 3 and 4 are axial sections of the first and second parts of the apparatus respectively, FIGS. 5 and 6 are side elevational views corresponding to FIGS. 3 and 4 respectively as seen from the respective directions A, B.

FIG. 7 is a cross-section on a larger scale in the plane CC of FIG. 4,

FIGS. 15 and 16 are axial sections at 90° to one another of the part of the main duct contained in the handle, FIGS. 17 and 18 show in an analogous manner the upper part of two specific rigid instruments, FIGS. 15

DESCRIPTION OF A PREFERRED EMBODIMENT

Figures 1, 2:
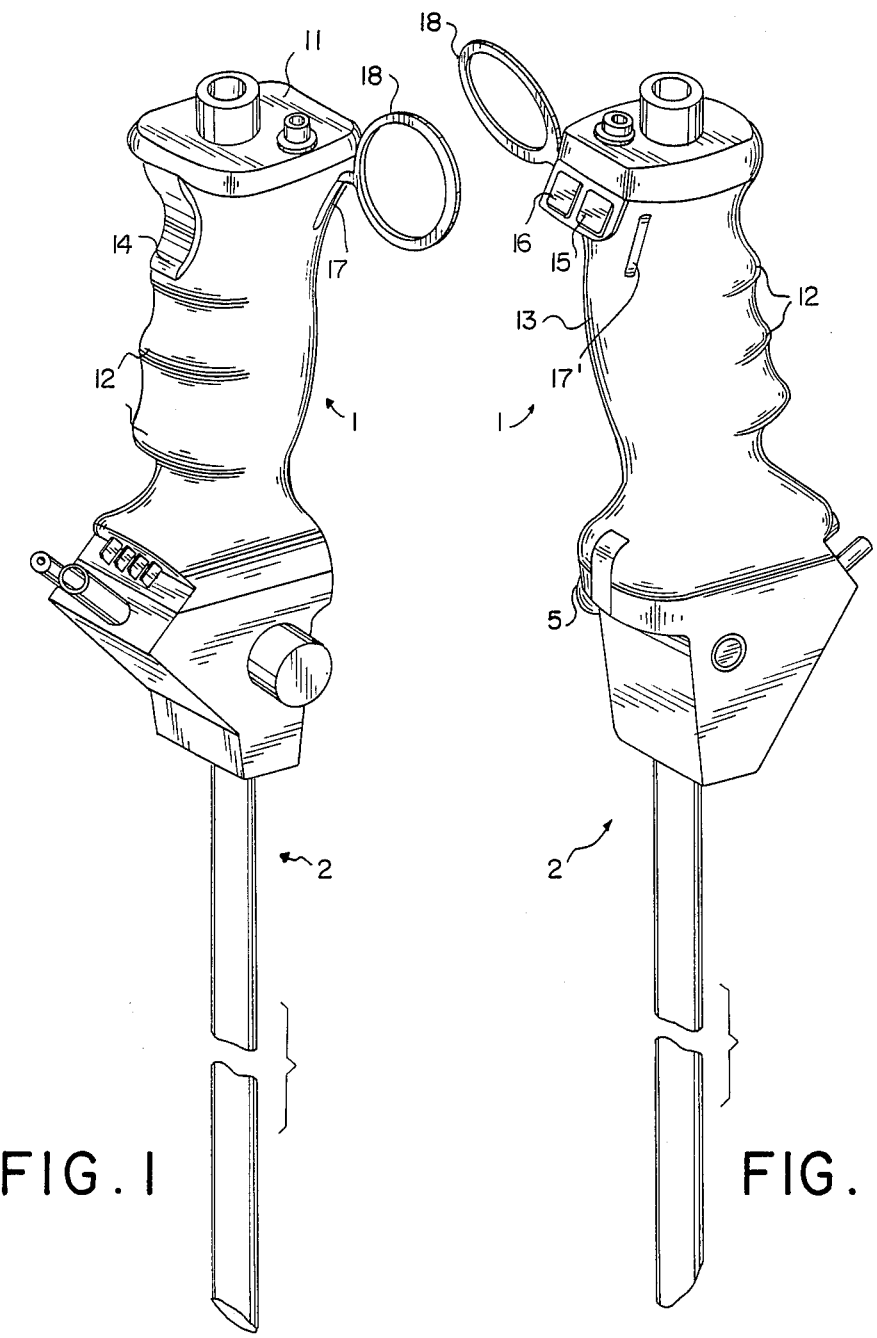
FIGS. 1 and 2 are perspective views from two different angles of a surgical apparatus according to the invention.
Figure 8:
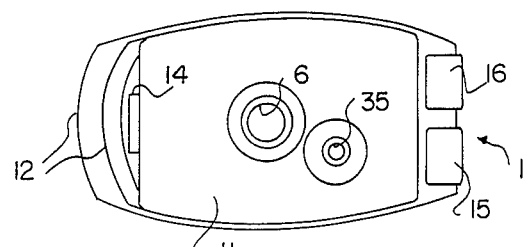
FIG. 8 is a plan view of the first part as seen from the direction D of FIG. 5.

In FIGS. 1 to 6, the preferred embodiment of the surgical apparatus according to the invention can be seen to be composed of two parts 1 and 2, referred to respectively as the handle and canula, which can be connected to one another in their axial extension. The connection is made on two connecting faces, 3,3' by means of a "quarter-turn" bayonet connector 4,4' with a helical ramp, a ratchet locking mechanism 5 maintaining the parts 1 and 2 in the connected position.

The first, upper part of the apparatus is constituted mainly by a first guide tube section 6 surrounded by the handle 8. The handle has the general shape of an elongate parallelepiped inclined at about fifteen degrees relative to the axis 9 of the main tube, the lower face 3 and the upper face 11 being perpendicular to the axis. The handle is a hollow body in two moulded parts supporting or containing various control members; the ergonomic shape of the handle may be noted, in particular the fingergrip mouldings 12 on the anterior face and the smooth, curved shape of the posterior part 13, ensuring accurate positioning of the handle relative to the fingers and to the palm of the hand. The control members supported by the handle are as follows: on the anterior face, a detent 14 which can be actuated by the index finger controls the connection to power either of a thermal or electric coagulator or of a laser generator, or of any other instrument associated with the apparatus; on the posterior face, a pair of push-buttons 15 and 16 respectively control the aspiration and injection of irrigation liquid; it is important to note that, these two push-buttons being adjacent, they can be actuated simultaneously as well as separately by the thumb; on each of the lateral faces, a port 17, 17' allows the passage of a lever 18 for manual control of instruments which are either rigid or flexible, it being possible for these levers to be fitted either for the right hand or for the left hand. A channel 10 for the passage of electrical connection cables will also be noted.

The second, lower part of the apparatus the canula 20 and a connecting piece 21 constructed integral with the canula. According to another embodiment, the canula could be a part which can be separated from the connecting piece). The connecting piece 21 has the shape of a prism with polygonal faces 23 and 24, one of the lateral faces constituting the connecting face 3,, another lateral face having a recess 25 for the engagement of the ratchet 5 and another lateral face 26 possessing two nozzles 27 and 28 for the passage of fluids.

In FIG. 7 it can be seen that the canula is composed of an outer tube or jacket 30 surrounding three ducts separated by a ceramic or plastic material 31. The largest duct has a section of complex shape comprising a circular central part 32 and two eccentric lateral parts 33; the central part forms a guiding duct 32 for rigid instruments which are themselves of circular section; the two lateral parts 33 constitute return ducts for irrigation or aspiration. Another of the narrower ducts is an irrigation duct 34, while the third is a passage duct 35 for flexible instruments.

With reference more particularly to FIGS. 3, 4, 7, 8, 9 and 10, it can be seen that the guiding duct 32 seperates, into a lateral duct 41 which terminates outside the connecting piece 21. A slide valve 37 provided with a bore 42 is arranged across the axial duct 36 in order to open or close the axial duct under the action of a pushbutton 38 against a spring 39. The irrigation duct 34 forms an elbow (FIG. 9) to rejoin the nozzle 27; this nozzle 27 incorporates a ball valve 40 which can only open against a spring if a sufficient pressure of irrigation liquid is applied to the nozzle.

Figure 9:
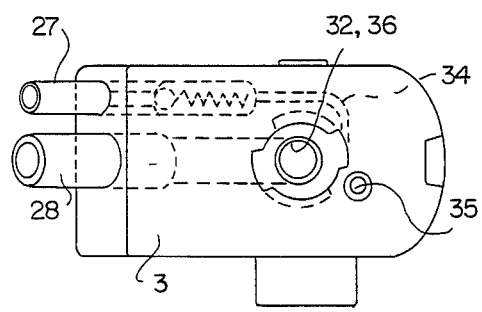
FIG. 9 is a plan view in the direction E of FIG. 6.
Figure 10:
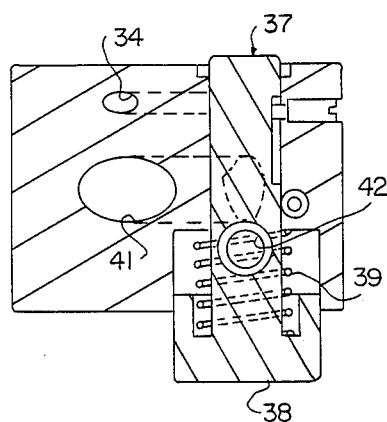
FIG. 10 is a cross-section in a plane FF of FIG. 6.
Figure 11:
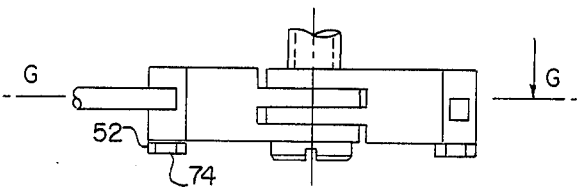
FIG. 11 shows, on a greatly enlarged scale, the articulation of the lever which is visible in FIGS. 3 and 5.
Figure 12:
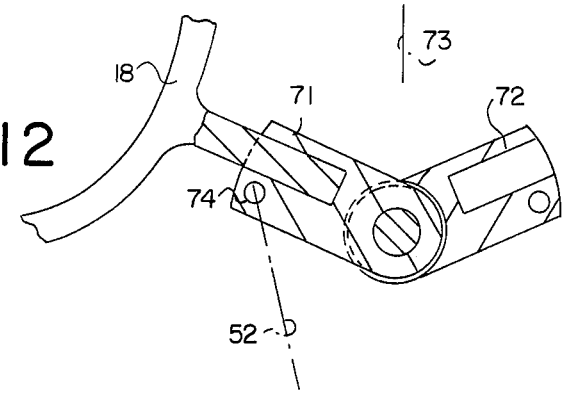
FIG. 12 is a partial section in a plane GG of the preceding figure.
Figure 14:
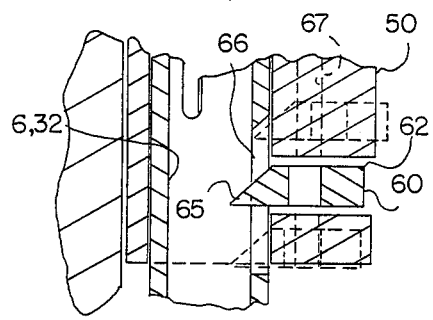
FIG. 14 is a fragmentary axial section corresponding to FIG. 13 in the plane G of the latter figure.
Figure 13:
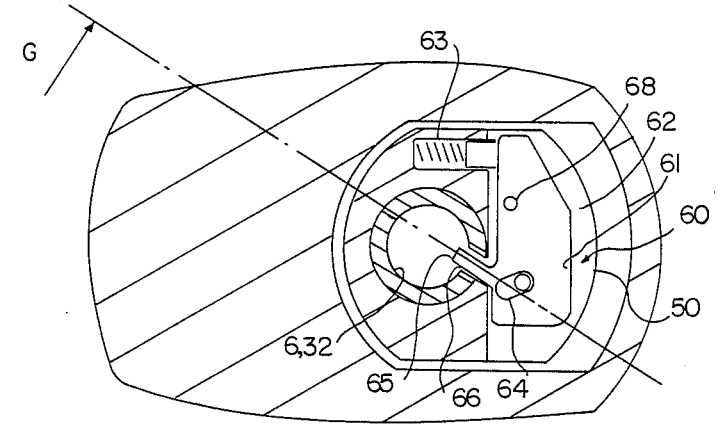
FIG. 13 is a section, on a larger scale than that of FIG. 3, in a transverse plane H of that figure.

FIG. 9 shows how the duct 35 for flexible instruments terminates at the connecting face 3', this duct also terminating (FIG. 8) at the upper end face 11 of the handle 1.

An explanation will be given, more particularly with reference to FIGS. 11 to 18, of the manipulation of various instruments which can be used with the apparatus. The means of manipulation essentially comprise a slider 50 which can be displaced axially and reciprocally by the lever 18 and a rod 52 connecting the slider to the lever (FIG. 3).

The slider can grip instruments of two categories: rigid instruments capable of being introduced into the guiding duct 6, 32 and flexible instruments capable of being introduced into the passage duct 35.

The grip of the slider on the flexible instruments is brought about by means of a coupling mechanism 60 which comprises a latch 61 in a lateral recess 62 of the slider and mounted to pivot about an axis 68 against a spring 63. The latch has an oblong aperture 64 and a sensor finger 65 intended to project through a port 66 into the interior space of the guiding duct 6, 32. The slider 50 is itself pierced by an axial duct 67 situated in the extension of the passage duct 35; by pivoting the latch, the aperture 64 can be placed opposite the duct 66, when a rigid instrument which is present in the guiding duct 6, 32 pushes back the sensor finger 65; if a flexible instrument is present in the duct 35 and in the axial duct 67 of the slider, and if no rigid instrument is present in the guiding duct 6, 32, then the latch exerts pressure on the flexible instrument and couples the latter to the slider; hence reciprocal manipulation of the slider will produce reciprocal movement of the flexible instrument. Examination of FIG. 14 will also show that the upper position of the slider, by virtue of the inclined-plane shape of the sensor finger 65, necessarily releases the flexible instrument. The slider 50 is permanently stressed in the upper position by a spring 75 (FIG. 3). The result of all these arrangements is that a flexible instrument and a rigid instrument which are incompatible can never project together in an undesired manner at the lower end of the canula.

Returning to FIGS. 11 and 12, it will be seen that the lever 18 is mounted in the extension of one of two lever arms 71, 72 articulated about an axis 73, the shaft on which the lever is mounted itself being articulated on the rod 52 about an axis 74.

The grip of the slider rigid instruments, as can clearly be seen in FIGS. 15 to 18, is achieved by means of a pair of interior pins 80, projecting slightly within the guiding duct 6, 32 through a pair of ports 81 (FIGS. 15, 16). FIGS. 17, 18 more particularly illustrate the upper part of a rigid instrument comprising a head 85 fixed to a tube 86 extending into the vicinity of the end of the instrument (not shown in the figure). A stem 87 can slide within the tube 86 and extends into the vicinity of the end of the instrument; the tube 86 and the stem 87 are connected respectively to one jaw of the functional part of the instrument, for example the jaw of cutting or gripping forceps. The stem 87 is connected by a pin 88 to a tubular member 89 surrounding the tube 86 and passing through a pair of ports such as 90 in the latter; thus the movement of the tubular member 89 along the tube 86 brings about a corresponding movement of the stem 87 within the latter. It will be noted that the movements of the parts described above cannot be other than axial movements, rotation being prevented by the pin and the ports 90. The tubular member is provided with a pair of longitudinal grooves such as 91 which are diametrically opposed and each terminate in a transverse groove 93, the groove comprising each longitudinal groove 91 and transverse groove 93 forming an inverted L-shaped groove. The introduction of a rigid instrument through the upper orifice 94 of the apparatus is achieved by sliding the grooves 91 of the tubular member along the pins 80 and then causing the head of the instrument to rotate through 90°. In the course of this rotational movement claws 95 on the head of the instrument to engage the ramps 96 at the tip of the aperture 94, such as a "quarter-turn bayonet" tip of a known type. In this latter position, the pins 80 in the base of the transverse grooves 93 of the tubular member 89 will entrain this member in a displacement corresponding to that of the slider 50 under the control of the lever 18 (FIGS. 1 and 2). It should be noted, with reference also to FIG. 10, that the presence of the tube 86 in the bore 42 of the slide of the valve ensures leak-tight separation between the lower and upper parts of the apparatus.

Figure 19:
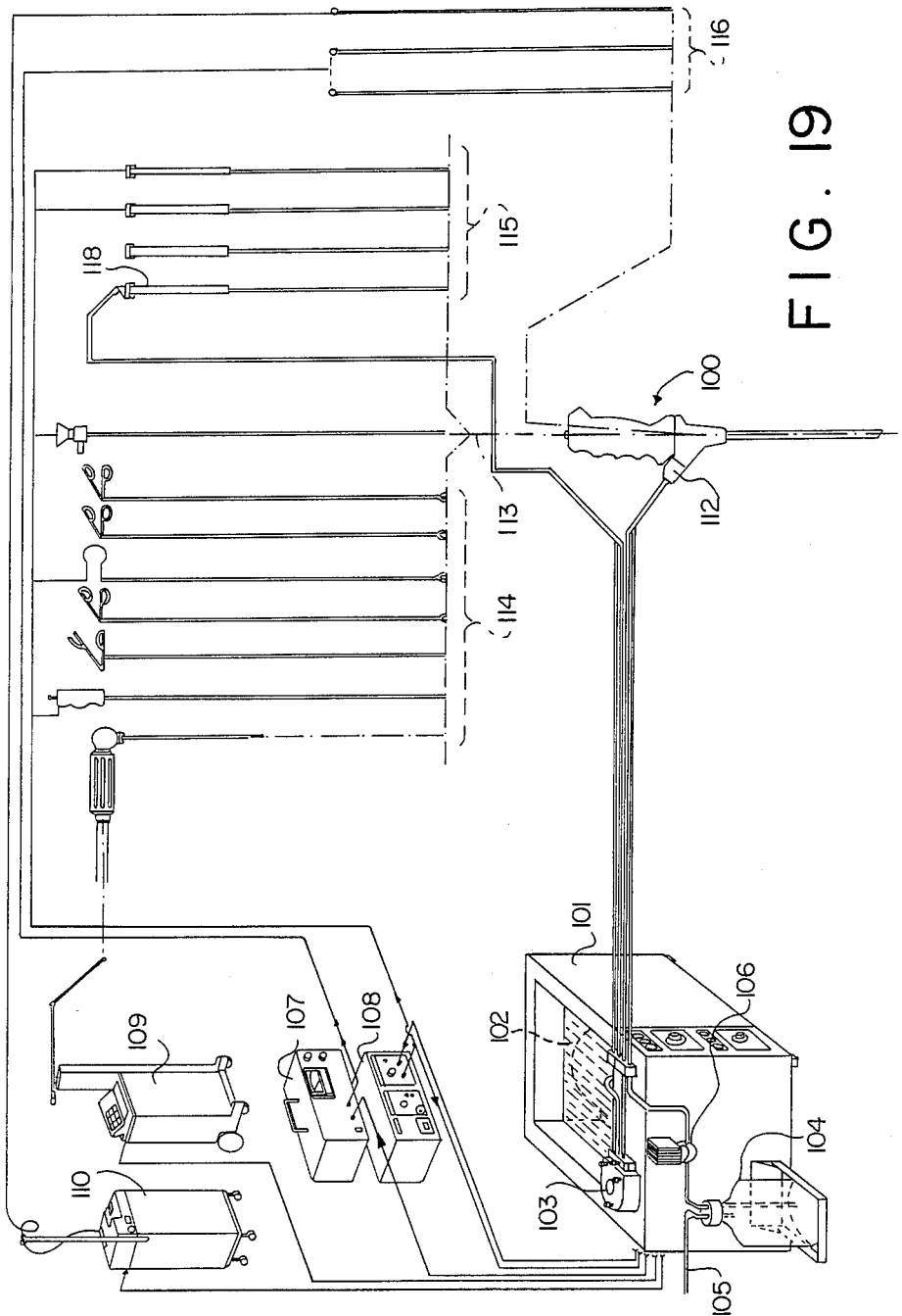
FIG. 19 is a diagrammatic representation of the entire installation and of various accessories which can be used with the multi-functional instrument according to the invention.

The installation shown in FIG. 19, which permits optimum utilization of the apparatus 100 according to the invention, combines a conditioning unit for the irrigation fluid, a unit for aspirating and receiving the liquids and tissues obtained by puncturing, and all the principle irrigation, aspiration, electrocoagulation and laser-ray generation controls.

The irrigation fluid conditioning unit comprises a double boiler 101 containing one or more flexible bags such as 102 for sterile storage of irrigation fluid. Peristaltic pumps such as 103 draw from these bags and deliver the fluid to nozzles such as 27 described above, or to other instruments such as the instrument 118. In addition, supported by the double boiler, a receiving bottle 104 is associated with a vacuum source 105 and one or more solenoids such as 106 connected to nozzles such as 28 described above.

The installation further comprises feeds 107 and 108 for the electrocoagulation or thermocoagulation instruments, and generators 109 and 110 for generating laser beams of the $CO_2$ or Yag type.

It will be noted that the apparatus 100 possesses a connecting block 112 providing the connection of the apparatus not only for intakes and outputs of fluids but also for electrical controls originating from various control members carried by the handle. All the electrical controls are of low direct voltage (DC 24 V).

Finally, FIG. 19 groups the instruments which can be used by the apparatus into two categories: firstly, a group of rigid instruments 113 subdivided into conventional instruments 114 and instruments referred to as specific 115, the latter being of the type shown in FIGS. 17, 18, and secondly flexible instruments 116, the flexible instruments and the conventional rigid instruments being known in the art of operative coelioscopy.

Although a particular embodiment of a multifunctional apparatus according to the invention has been described, it must be understood that the scope of the said invention is not restricted to this embodiment but extends to any apparatus possessing the general characteristics defined above.

We claim:

1. Operative coelioscopy surgical apparatus for receiving electrical instruments, flexible mechanical instruments and rigid mechanical instruments, the apparatus comprising, in combination:
   a tubular canula for receiving said instruments and for permitting the passage of irrigation fluid and body fluid therethrough; and
   a handle removably connected to the canula and having a plurality of manually operable control means, said control means being operable either simultaneously or separately and including
   first means for controlling the transmission of irrigation fluid through the canula,
   second means for controlling the aspiration of body fluid through the canula,
   third means for the electrical control said electrical instruments, and
   fourth means for controlling said flexible mechanical instruments and said rigid mechanical instruments.

2. Operative coelioscopy surgical apparatus as claimed in claim 1, the canula including an integrally formed connector for attaching the canula to the handle, the connector having a polygonal prism configuration with a lateral face in abutting relationship with the handle.

3. Operative coelioscopy surgical apparatus as claimed in claim 1, the canula defining a first duct for the passage of irrigation fluid, a second duct for the passage of flexible mechanical instruments, and a third duct for the passage of rigid mechanical instruments and evacuation fluid.

4. Operative coelioscopy surgical apparatus as claimed in claim 3, the third duct having a first branch for receiving rigid mechanical instruments and a second branch for receiving evacuation fluid.

5. Operative coelioscopy surgical apparatus as claimed in claim 4, which further comprises, in combination:
   a first nozzle communicating with the second branch of the third duct for receiving evacuation fluid;
   a second nozzle communicating with the first duct for receiving irrigation fluid; and
   unidirectional valve means associated with the second nozzle for limiting the direction of flow of the irrigation fluid.

6. Operative coelioscopy surgical apparatus as claimed in claim 4, in which the third duct further includes at least one lateral passage for evacuation fluid.

7. Operative coelioscopy surgical apparatus as claimed in claim 1, the handle having a longitudinal axis inclined at an angle of about 15° relative to the axis of the tubular canula.

8. Operative coelioscopy surgical apparatus as claimed in claim 1, the handle having an elongate parallelepiped shape with a connecting face abutting the canula, a posterior face, an anterior face and at least one lateral face; at least one push-button on the posterior face of the handle; another push-button on the anterior face of the handle; and an operating lever on said lateral face.

9. Operative coelioscopy surgical apparatus as claimed in claim 8, which further comprises slider means connected to the operating lever for controlling the movement of an instrument in the tubular canula.

10. Operative coelioscopy surgical apparatus as claimed in claim 9, which further comprises a coupling mechanism connected to the slider means to enable reciprocable manipulation of a flexible instrument in the tubular canula in response to actuation of the operating lever.

11. Operative coelioscopy surgical apparatus as claimed in claim 1, which further comprises a bayonet connector for removably connecting the canula to the handle.

* * * * *